US006997178B1

(12) United States Patent
Reynaud

(10) Patent No.: US 6,997,178 B1
(45) Date of Patent: Feb. 14, 2006

(54) OXYGEN INHALER MASK WITH SOUND PICKUP DEVICE

(75) Inventor: Gérard Reynaud, Bordeaux (FR)

(73) Assignee: Thomson-CSF Sextant, Velizy Villacoublay (FR)

( * ) Notice: Subject to any disclaimer, the term of this patent is extended or adjusted under 35 U.S.C. 154(b) by 0 days.

(21) Appl. No.: 09/831,899

(22) PCT Filed: Nov. 19, 1999

(86) PCT No.: PCT/FR99/02853

§ 371 (c)(1),
(2), (4) Date: May 24, 2001

(87) PCT Pub. No.: WO00/30716

PCT Pub. Date: Jun. 2, 2000

(30) Foreign Application Priority Data

Nov. 25, 1998 (FR) .................................. 98 14854

(51) Int. Cl.
*A61B 18/08* (2006.01)

(52) U.S. Cl. ............................ 128/201.19; 128/206.21

(58) Field of Classification Search ........... 128/201.19, 128/206.21, 206.18
See application file for complete search history.

(56) References Cited

U.S. PATENT DOCUMENTS 2,950,360 A * 8/1960 Duncan ...................... 381/176
3,314,424 A * 4/1967 Berman ................. 128/201.19
3,633,705 A * 1/1972 Teder ......................... 181/158
3,910,269 A * 10/1975 Ansite et al. .......... 128/201.24
4,072,831 A * 2/1978 Joscelyn ..................... 381/367
4,352,353 A * 10/1982 Bolton et al. .......... 128/201.23
4,539,983 A 9/1985 Angell
4,718,415 A * 1/1988 Bolnberger et al. .... 128/201.19
4,901,356 A * 2/1990 Bauer ......................... 381/367
4,961,420 A * 10/1990 Cappa et al. .......... 128/201.19
5,195,528 A 3/1993 Hok
5,503,141 A * 4/1996 Kettl et al. ............ 128/201.19
5,572,990 A * 11/1996 Berlin ................... 128/201.19
5,829,431 A * 11/1998 Hannah et al. ........ 128/201.19
5,860,417 A * 1/1999 Kettl et al. ............ 128/201.19
5,987,142 A 11/1999 Courneau et al.
6,058,194 A 5/2000 Gulli et al.
6,128,594 A 10/2000 Gulli et al.

FOREIGN PATENT DOCUMENTS

| | | |
|---|---|---|
| EP | 0 377 316 | 7/1990 |
| EP | 0 686 408 | 12/1995 |
| EP | 0 771 577 | 5/1997 |
| WO | WO 97/37724 | 10/1997 |

* cited by examiner

*Primary Examiner*—Anhtuan T. Nguyen
*Assistant Examiner*—Darwin P Erezo
(74) *Attorney, Agent, or Firm*—Oblon, Spivak, McClelland, Maier & Neustadt, P.C.

(57) ABSTRACT

Oxygen breathing masks with a sound pickup device. A microphone capsule of the sound pick-up device is positioned at the base of a mouth-piece whose aperture is placed just before the mask user's mouth. Such a mask may find particular application for aircraft pilots.

25 Claims, 4 Drawing Sheets

OXYGEN INHALER MASK WITH SOUND PICKUP DEVICE

BACKGROUND OF THE INVENTION (1) Field of the Invention

The present invention relates to oxygen breathing masks with an associated sound pick-up device, these masks being used especially by fighter aircraft pilots.

(2) Description of Related Art

Masks of this kind are known and one of them shall be described here below.

The prior art masks are acoustically unsatisfactory when the conditions of use are poor or when specific operations, such as voice recognition, have to be implemented.

The aim of the present invention is to improve existing masks in order to improve their acoustic characteristics.

This is obtained especially by modifying the sound pick-up mechanism within the mask.

BRIEF SUMMARY OF THE INVENTION

According to the invention, there is proposed an oxygen breathing mask with sound pick-up device comprising a flexible cap with a respiratory aperture pierced through it and a microphone capsule positioned above the aperture, characterized in that the mask comprises a mouth-piece, this mouth-piece being mounted in front of the capsule, with its aperture turned towards the location at which the pilot's mouth gets positioned in the mask and, taking this position of the mouth into consideration, in that the mouth-piece has its axis passing substantially through the junction line of the lips and its aperture is substantially parallel to the labial plane, namely to the plane tangential to the two lips, just before the mouth.

BRIEF DESCRIPTION OF THE DRAWINGS

The present invention will be understood more clearly and other features shall appear from the following description and the appended figures, of which.

In the different figures, the corresponding elements are designated by the same references.

DETAILED DESCRIPTION OF THE INVENTION

Figure 1:
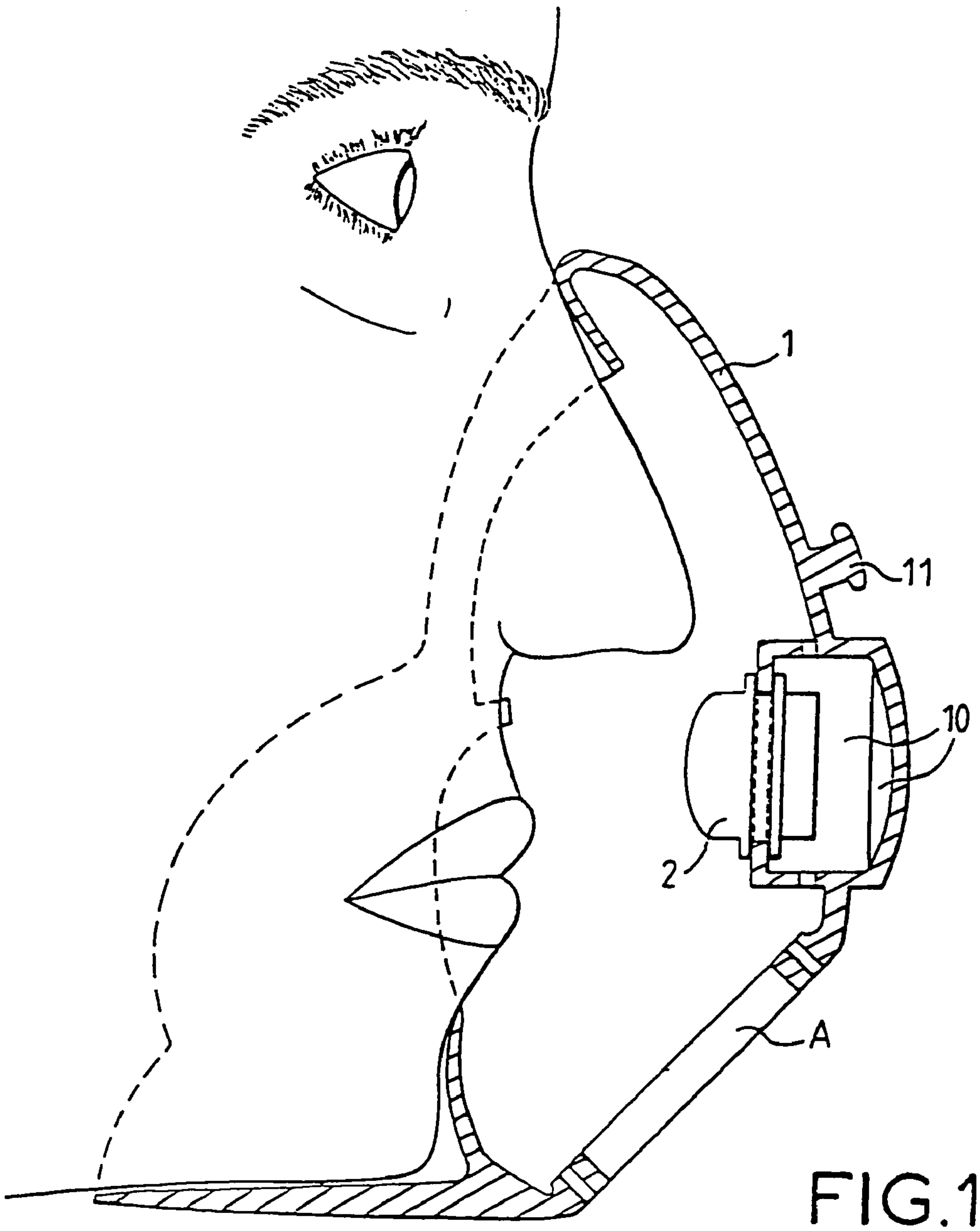
FIG.1 PRIOR ART
FIG. 1 shows a mask according to the prior art.

FIG. 1 gives a side view of a face of a pilot and, on his face in a vertical sectional view, the flexible cap 1, made of natural rubber, of an oxygen-breathing mask. In the representation according to FIG. 1, as also in the representations according to FIGS. 2 and 3, only the cap is seen in a section. Similarly in FIG. 1 and FIGS. 2 and 3, the rigid shell that covers the cap 1 on the side opposite the face has not been shown in order to simplify the drawing and also because it makes no contribution to the understanding of the invention.

With respect to a horizontal plane passing through the pilot's lip line, the cap is pierced with a 34 mm diameter hole A located beneath this plane, and comprises a microphone capsule housing 10 located above this plane.

The hole A constitutes the exhalation port of the cap. It enables the mounting of an exhalation valve that is not shown. The respiratory port of the mask is placed on the left-hand side of the cap.

The housing 10 is a sort of cavity whose walls form a first protrusion and second protrusion, respectively on the external wall and internal wall of the cap. The first protrusion is closed while the second protrusion is pierced with a cylindrical hole. A microphone capsule 2, commercially distributed by the firm Silec under reference S4045, is overlaid in a second protrusion where it is stands supported on the edges of the cylindrical hole.

A catch 11, perpendicular to the external wall of the cap, is a means of holding the cap in the shell. This catch is mushroom-shaped and the cap is placed flat against the internal surface of the shell with the stem of the "mushroom" passing through a hole of the shell and the head of the "mushroom" placed flat against the external surface of the shell. This catch, as also the walls of the housing 10, is made out of the same material as the rest of the cap.

The assembly of FIG. 1 has various flaws, especially: excessive sensitivity to parasitic noises, limited non-flat passband beyond 4 kHz, tendency to acoustic saturation when the pilot speaks loudly, etc.

In a first implementation of the mask according to the invention, it has been proposed to improve the acoustic functioning while, at the same time, keeping the original cap. For this purpose in particular, quite naturally a search was made for more efficient microphone capsules but, above all, the position of the capsules in the cap was redesigned, means were implemented to concentrate the useful acoustic emissions on the capsule and other means were designed to limit the phenomena that could lead to the saturation of the capsule and limit the noises linked to the helmet such as noises of the opening and closing of clack valves and oxygen intake and exhalation valves.

Figure 2:
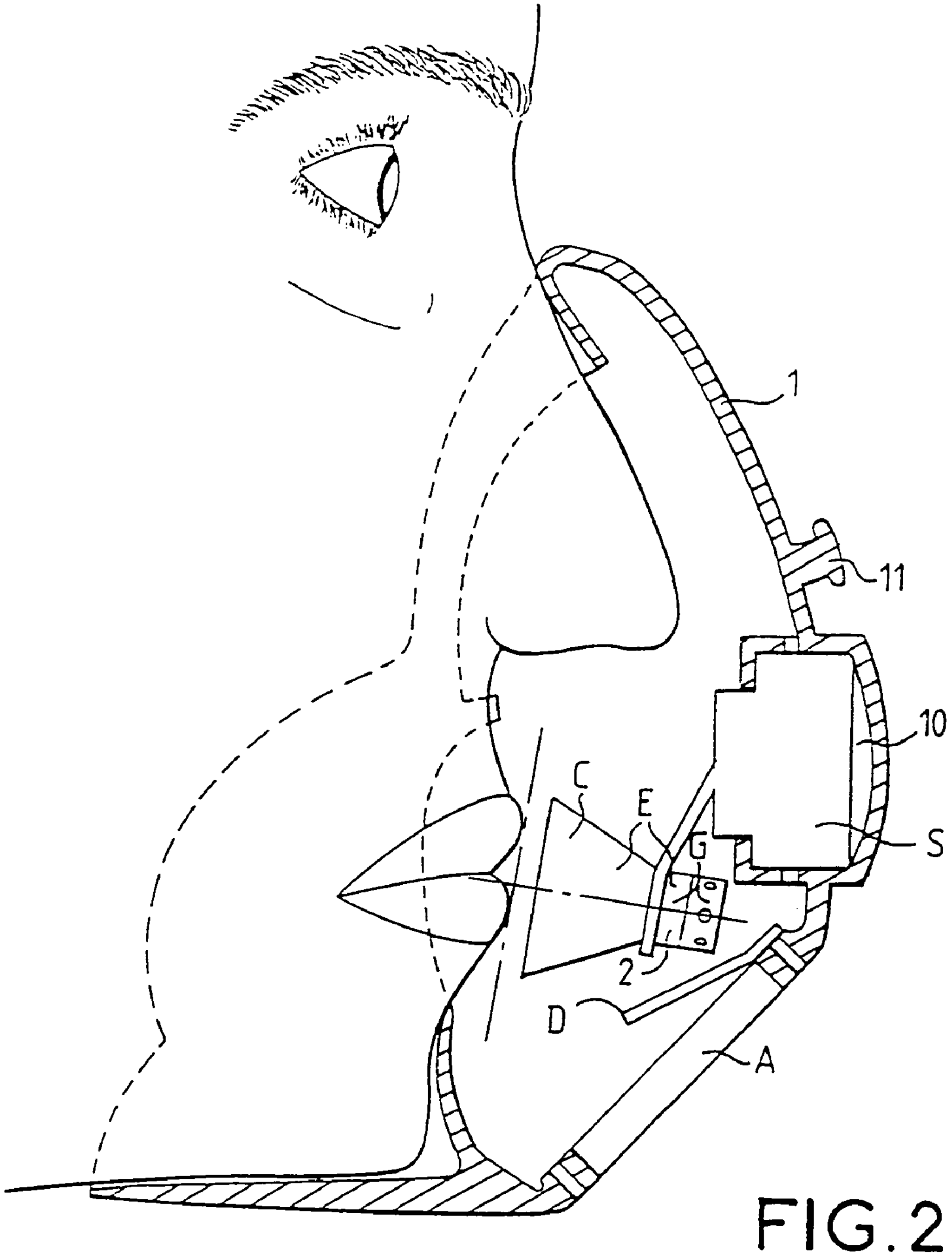
FIG. 2 shows a first mask according to the invention.

FIG. 2 is distinguished from FIG. 1 only with respect to the microphone part. Indeed, the cap 1 remains unchanged but the microphone capsule is no longer overlaid in the housing 10. Instead, there is a matching piece S that partly penetrates the housing in which it is fixed. The part of the element S outside the housing has an arm at the end of which there is mounted a microphone assembly, E, with a mouth-piece C and, behind the mouthpiece, an acoustic chamber G whose side wall is pierced with holes. Inside the chamber, there is a microphone capsule 2 commercially distributed by the firm Panasonic under the reference WM53. The holes pierced in the chamber improve the working of the capsule by achieving a high-pass filtering with a cutoff frequency in the range of 100 Hz.

It must be noted that the axis of the mouth-piece shown by an axis line in FIG. 2 passes substantially through the pilot's lip-junction line and that the aperture of the mouth-piece is located in a plane substantially parallel to the labial plane, namely the plane tangential to the two lips, just in front of the mouth. The labial plane is perpendicular to the plane of FIG. 2, and its trace in the plane of FIG. 2 has been drawn with axis type lines.

In order to limit the entry, into the capsule, of the disturbing noises caused by the opening of the exhalation valve positioned in the port A, when the user speaks, a baffle, D, consisting of an aluminum plate is interposed between the location of the capsule 2 and the port A. This plate is screwed into the cap 1 at its upper ridge located slightly above the port A.

Figure 3:
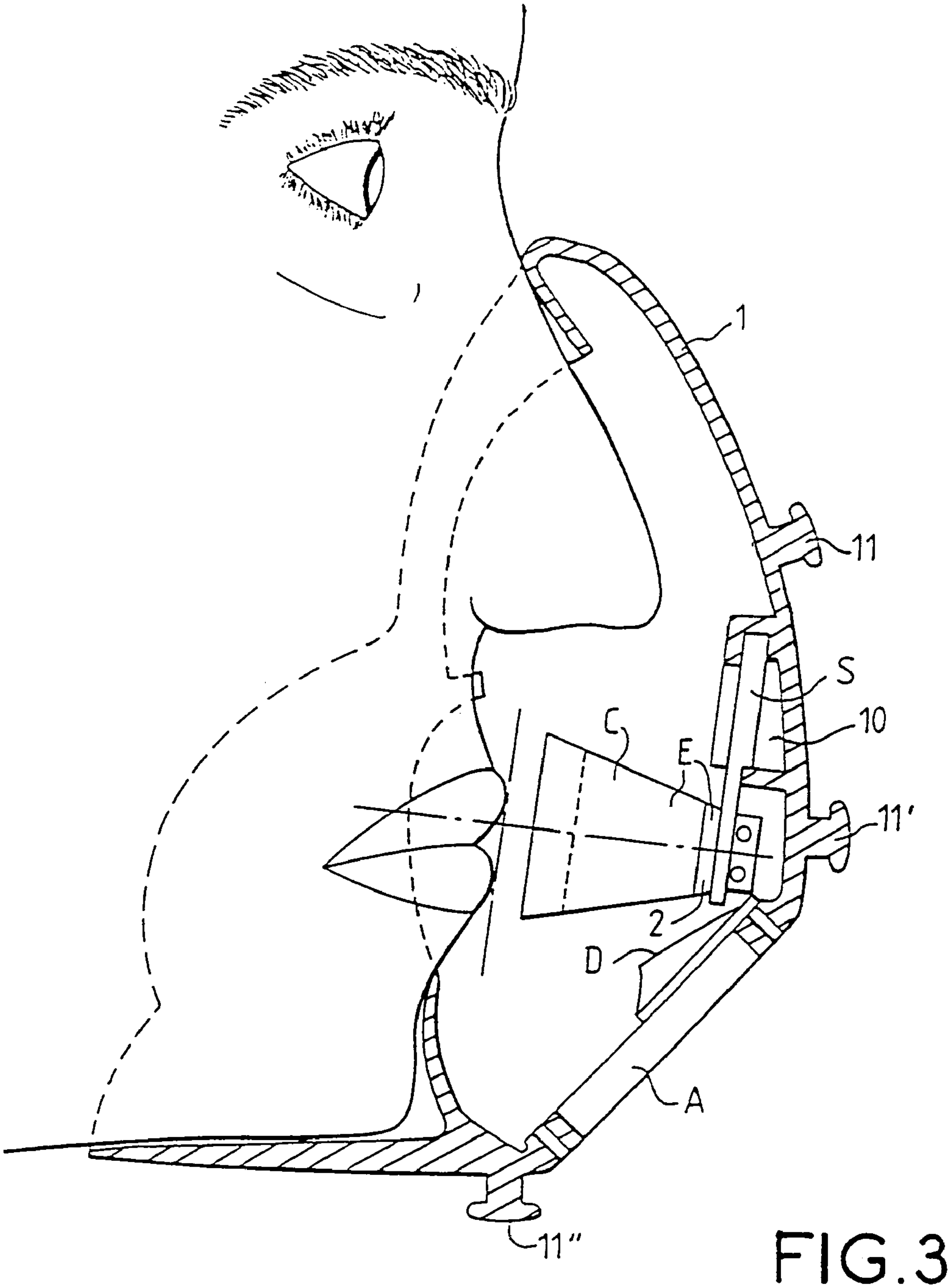
FIG. 3 shows a second mask according to the invention.

A second implementation of the mask according to the invention is illustrated in FIG. 3. In this case, it is no longer a mask according to the prior art, adapted to the invention, but a specially designed mask for the implementation of the invention.

The flexible cap 1 has been redesigned:

the housing 10 has been reduced in volume and no longer forms a protrusion on the external wall of the cap. This reduction in volume of the housing 10 increases the available space towards the bottom of the mask, permitting an optimal placing of the microphone assembly in the axis of the mouth, and making it possible to propose detachable mouth-pieces made in different sizes, namely in different mouth-piece heights in order to position the aperture of the mouth-piece in taking account of the morphology of the bottom of the mask user's face. In the example described, the mouth-piece is proposed in four different heights ranging from 10 to 18 mm. The goal is to make the distance between the lips and the mouth-piece as small as is permitted by the condition of avoiding discomfort according to which the lips should never be in contact with the mouth-piece. In FIG. 3, this possibility of choosing between several heights of mouth-pieces is illustrated by a first mouth-piece drawn in solid lines adapted to the position of the user's lips and a second mouth-piece in a withdrawn position with respect to the first one, the front of this second mouth-piece being shown by dashes;

six additional catches, of which two 11' and 11" appear in FIG. 3, have been added. These six catches have the same shape and constitution as the catch 11 and, like the catch 11, they are perpendicular to the external face of the cap. The catches 11 and 11' are located on either side of the port A. Two of the other four catches are located on the left flank of the cap on either side of the respiratory port while the last two catches are located on the right flank of the cap, symmetrically with respect to the two catches of the left flank. These additional catches hold the cap more securely inside the shell and reduce the low-frequency parasitic vibrations of the cap and therefore the disturbances that they produce in the microphone capsule, especially when the user of the mask is speaking.

Figure 4A:
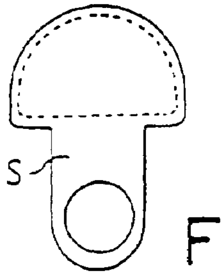
FIGS. 4*a*, 4*b*, 5*a*, 5*b*, 5*c*, 5*d* and 6*a*, 6*b* show views of elements proper to the mask according to FIG. 3.
Figure 4B:

The reduction of the volume of the housing 10 leads to a corresponding reduction of the part of the matching piece S that penetrates the housing 10. FIGS. 4*a*, 4*b* show this matching part seen in a top and side view, with an upper bowl-shaped part and a lower part with a cylindrical hole pierced through it.

Figure 5A:
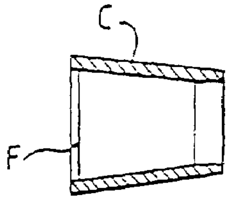
Figure 5B:
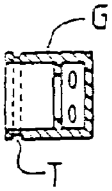
Figure 5C:
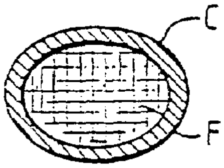

The microphone assembly E is practically unchanged. However, we must note the addition of an acoustic screen F at the aperture of the mouth-piece. This acoustic screen consists of a fine metal lattice made of stainless steel. It must be noted that the acoustic screen may be constituted conventionally by foam or fabric but that these materials are less well suited to being used in a mask. FIGS. 5*a*, 5*b*, 5*c* pertain to this microphone assembly comprising: the mouth-piece referenced C with the acoustic screen, referenced F, and the acoustic chamber, referenced G, with its front part constituting the housing for the microphone capsule and its rear part being laterally pierced with holes. FIG. 5*a* is a longitudinal sectional view of the mouth-piece C with the screen F. FIG. 5*b* is a view, also in a longitudinal section, of the acoustic chamber G. This figure shows a circular groove T surrounding the chamber G in its front part. This groove T serves as the housing for an O-ring that is not shown. This O-ring is designed to provide an efficient mechanical link between the mouth-piece and the chamber after these two parts are fitted into each other. This solution enables the mouth-piece to be easily assembled and disassembled, without tools, for maintenance operations. It must also be noted, as can be seen in FIG. 5*c*, that the mouth-piece has an elliptically sectioned aperture whose biggest dimension is parallel to the user's lip junction line.

Figure 5D:
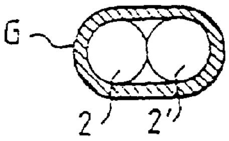

FIG. 5*d* is a sectional view, perpendicular to the axis of the mouth-piece, pertaining to the microphone assembly if this assembly has not just one microphone capsule at the base of the mouth-piece but two capsules 2, 2'. This is possible because of the small size of the capsules used. The two capsules are mounted side by side in a space whose biggest dimension is horizontal and parallel to the user's lip junction line. It must be noted that FIGS. 5*a*, 5*b*, 5*c* are the same for a microphone set with one capsule and for a microphone set with two capsules. It must also be noted that, in the case of two capsules, each capsule is connected to the on-board electronic circuitry by a different pair of wires. In certain applications, this gives a replacement capsule for cases of malfunctioning of the commonly used capsule. In other applications it makes it possible to dedicate one of the two capsules to a voice command system. Naturally, in the event of a microphone set with two capsules, the matching piece 5 according to FIGS. 4*a*, 4*b* must be modified. Its lower part pierced with a hole must be widened and the hole must be enlarged so that the rear part of the microphone assembly E can be introduced therein.

Figure 6A:
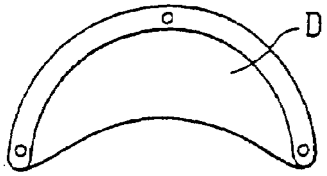
Figure 6B:

The baffle D has been improved. It is no longer a practical flat part but a curved part better suited to its role of acoustic screen. FIG. 3 shows the baffle D in a side view. Two FIGS. 6*a* and 6*b* again show the baffle but respectively in a top and side view, with this second side view that is at right angles to the first one and is taken from the cap 1 side located below the baffle. FIG. 6*a* shows three holes used to fasten the deflector in the cap 1 by means of screws. These holes are distributed on a flat half-collar whose concave edge is the convex edge of a curved crescent-shaped part.

Figure 7:
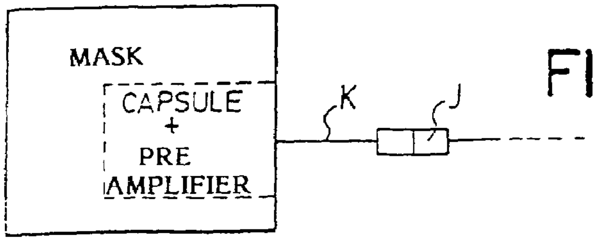
FIGS. 7 and 8 show two drawings respectively pertaining to the masks according to FIGS. 1 on the one hand and 2, 3 on the other.
Figure 8:
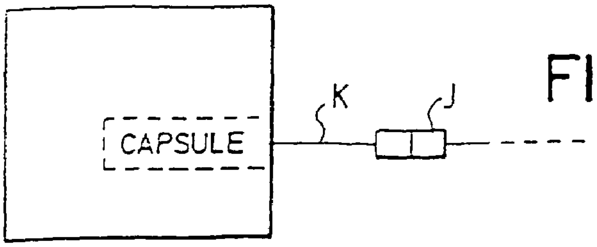

FIGS. 7 and 8 are two representations of a block diagram type respectively pertaining to a mask according to the prior art and according to the invention. In the case of FIG. 7, with a pilot's mask fitted out with a Silec S4045 microphone capsule, the signals given by the capsule are very low in level and have to be amplified in a preamplifier before they are transmitted through a connection cable K provided with a connector J to the electronic circuitry of the aircraft. It must be noted that the connector used for the pilot's mask is a releasable connector in the sense that the two complementary connection pieces, one male and one female, that form it get separated in the event of high tensile force on the connecting cable. In FIG. 8, with the pilot's mask fitted out with a Panasonic WM53 microphone capsule, the signals given by the capsule have a sufficient level not to require any preamplifier between the capsule and the connection cable K provided with its releasable connector J.

The present invention is not limited to the examples described but relates to all breathing masks provided with a microphone device with a mouth-piece whose aperture is placed before the pilot's mouth.

What is claimed is:

1. Oxygen breathing mask with a sound pick-up device, comprising:

a flexible cap;

an exhalation port pierced through the flexible cap;

a housing on an inner surface of the flexible cap;

first and second microphone capsules positioned above the exhalation port;

a conical tubular mouth-piece extending from a first distal end disposed adjacent the flexible cap to a second distal end projecting away from the flexible cap, the first and second microphone capsules mounted at said first distal end of the tubular mouthpiece with the first and second microphone capsules positioned between the flexible cap and the mouth-piece, said second distal end of said tubular mouth-piece disposed away from the first and second microphone capsules and defining an aperture turned away from said flexible cap; and an arm having first and second ends, wherein the first end is disposed within the housing, and the arm extends from the housing and supports at the second end the tubular mouth-piece at said first distal end adjacent the first and second microphone capsules.

2. Mask according to claim 1, wherein the mask has a top, bottom and opposed sides, and the aperture of the mouth-piece is elliptical with a greatest dimension of the ellipse extending laterally toward the sides of the mask.

3. Mask according to claim 1, wherein the mouth-piece has an acoustic screen positioned in the aperture.

4. Mask according to claim 3, wherein the screen is constituted by a metal lattice.

5. Mask according to claim 1, further comprising a baffle fixedly joined to the flexible cap and positioned between the first microphone capsule and the exhalation port.

6. Mask according to claim 1, further comprising first and second cables and complementary connection pieces of releasable connectors, each connected to first ends of the first and second cables, wherein respective second ends of the first and second cables are directly connected to the first and second microphone capsules.

7. Mask according to claim 1, further comprising plural catches fixedly joined to the flexible cap and mounted substantially perpendicularly to an external face of the flexible cap.

8. Mask according to claim 1, wherein the first and second microphone capsules are mounted side by side on a base of the mouth-piece.

9. Mask according to claim 1, wherein said tubular mouth-piece has an opening at said distal end larger than an opening facing the microphone capsule.

10. Mask according to claim 1, wherein said first and second microphone capsules are disposed in an acoustic chamber having a plurality of holes.

11. Mask according to claim 10, wherein said acoustic chamber has a high-pass filtering capability with a cutoff frequency in the range of about 100 Hz.

12. Mask according to claim 1, wherein a height of said mouth-piece with respect to a location at which a user's mouth is adapted to be positioned in the mask is adjustable.

13. Mask according to claim 12, wherein said height varies from about 10 to about 18 mm.

14. Mask according to claim 1, wherein said aperture of said tubular mouth-piece is turned towards a center of a location at which a user's mouth is adapted to be positioned, said mouth-piece having a longitudinal axis passing substantially through the center of said location, and said aperture defining a plane which is substantially perpendicular to said longitudinal axis.

15. An oxygen breathing mask, comprising:

a flexible cap;

an exhalation port pierced through the flexible cap;

a housing disposed on an inner surface of the flexible cap, the housing being separate from the exhalation port;

a body mounted in the housing;

an arm having first and second ends and extending from the body;

a microphone assembly supported at the second end of the arm and comprising a conical tubular mouth-piece having first and second distal ends, an acoustic chamber connected at the second distal end of the mouth-piece and disposed adjacent the flexible cap, and at least two microphones disposed in the acoustic chamber, wherein the conical tubular mouth-piece extends from the first distal end connected to the acoustic chamber to the second distal end projecting away from the flexible cap.

16. Mask according to claim 15, wherein the mask has a top, bottom and opposed sides, and the aperture of the mouth-piece is elliptical with a greatest dimension of the ellipse extending laterally toward the sides of the mask.

17. Mask according to claim 15, wherein the mouth-piece has an acoustic screen positioned in the aperture.

18. Mask according to claim 17, wherein the screen is constituted by a metal lattice.

19. Mask according to claim 15, further comprising a baffle fixedly joined to the flexible cap and positioned between the at least two microphones and the exhalation port.

20. Mask according to claim 15, further comprising first and second cables and complementary connection pieces of releasable connectors, each connected to first ends of the first and second cables, wherein respective second ends of the first and second cables are directly connected to the at least two microphones.

21. Mask according to claim 15, further comprising plural catches fixedly joined to the flexible cap and mounted substantially perpendicularly to an external face of the flexible cap.

22. Mask according to claim 15, wherein the at least two microphones are mounted side by side on a base of the mouth-piece.

23. Mask according to claim 15, wherein the acoustic chamber comprises a plurality of holes.

24. Mask according to claim 23, wherein said acoustic chamber has a high-pass filtering capability with a cutoff frequency in the range of about 100 Hz.

25. Mask according to claim 15, wherein a height of said mouth-piece with respect to a location at which a user's mouth is adapted to be positioned in the mask is adjustable.

* * * * *